United States Patent [19]

Kameswaran

[11] Patent Number: 5,426,225
[45] Date of Patent: Jun. 20, 1995

[54] PERFLUOROALKANOYL AMINONITRILES

[75] Inventor: Venkataraman Kameswaran, Princeton Junction, N.J.

[73] Assignee: American Cyanamid Company, Wayne, N.J.

[21] Appl. No.: 175,845

[22] Filed: Dec. 30, 1993

[51] Int. Cl.$^6$ .................. C07C 233/15; C07D 263/30
[52] U.S. Cl. ..................................... 564/212; 548/225
[58] Field of Search ................. 564/212, 209, 213; 548/228, 225

[56] References Cited

U.S. PATENT DOCUMENTS

| | | | |
|---|---|---|---|
| 3,310,570 | 3/1967 | Middleton | 548/225 |
| 4,288,384 | 9/1981 | Walker | 504/291 |
| 4,335,053 | 6/1982 | Walker | 504/270 |
| 4,897,109 | 1/1990 | Martin | 504/337 |
| 5,010,098 | 4/1991 | Brown et al. | 514/426 |
| 5,028,256 | 6/1991 | Martin | 504/342 |
| 5,030,735 | 7/1991 | Addor et al. | 548/531 |
| 5,118,816 | 6/1992 | Doehner et al. | 548/565 |

FOREIGN PATENT DOCUMENTS 2095237 3/1991 United Kingdom .

OTHER PUBLICATIONS

Matier, W. L.; Owens, D. A.; Comer, W. T.; Deitchman, D.; Ferguson, H. C. Seidehamel, R. J.; Young, J. R. Journal of Medicinal Chemistry, 1973, 16, 901.

Poupaert et al, N-acyl-alphat-aminonitrles in the Pinner Reaction, CA 78:43335, Abstract, 1972.

Primary Examiner—Glennon H. Hollrah
Assistant Examiner—Deborah Lambkin
Attorney, Agent, or Firm—John W. Hogan, Jr.

[57] ABSTRACT

There are provided perfluoroalkanoyl aminonitrile intermediates and their use in a facile and efficient synthesis of 2-perfluoroalkyl-3-oxazolin-5-one. Said oxazolinone is a key intermediate in the preparation of insecticidal, acaricidal and nematocidal pyrrole compounds.

10 Claims, No Drawings

PERFLUOROALKANOYL AMINONITRILES

BACKGROUND OF THE INVENTION

Arylpyrrole carbonitrile compounds and derivatives thereof are highly effective insecticidal, acaricidal and nematocidal agents. In particular 2-aryl-5-trifluoromethylpyrrole-3-carbonitrile compounds and their derivatives have been found to have a broad spectrum of activity at very low rates of application with effectiveness against resistant species. U.S. Pat. No. 5,030,735 describes methods to prepare said pyrrole compounds on a manufacturing scale and includes the 1,3-dipolar cycloaddition of the appropriate 3-oxazolin-5-one with 2-chloroacrylonitrile. Heretofore the 3-oxazolin-5-one key intermediate has been prepared through the appropriate phenylglycine compound in a 4 step synthetic route from the preceding aminonitrile.

It is an object of this invention to provide perfluoroalkanoyl aminonitrile compounds useful in preparing 2-perfluoroalkyl-3-oxazoline-5-one.

It is a further object of this invention to provide a convenient source of a key intermediate in the manufacture of insecticidal, acaricidal and nematocidal arylpyrrole compounds.

SUMMARY OF THE INVENTION

There is provided a perfluoroalkanoyl aminonitrile intermediate of formula I $$R-\underset{\underset{CN}{|}}{CH}-NH-\overset{O}{\underset{||}{C}}-C_nF_{2n+1} \quad (I)$$

wherein n is an integer of 1, 2, 3, 4, 5, 6, 7 or 8;

R is 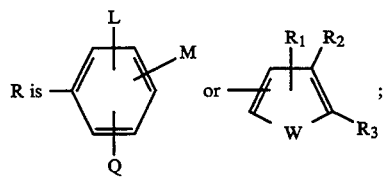 ;

L is hydrogen or halogen;

M and Q are each independently hydrogen, halogen, CN, $NO_2$, $C_1-C_4$alkyl, $C_1-C_4$haloalkyl, $C_1-C_4$alkoxy, $C_1-C_4$haloalkoxy, $C_1-C_4$alkylthio, $C_1-C_4$alkylsulfinyl or when M and Q are on adjacent positions they may be taken together with the carbon atoms to which they are attached to form a ring in which MQ represents the structure $-OCH_2O-$, $-OCF_2O-$ or
$-CH=CH-CH=CH-$ with the proviso that at least one of L, M and Q must be other than hydrogen;

$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

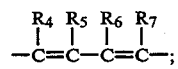

$R_4$, $R_5$, $R_6$ and $R_7$ are each independently hydrogen, halogen, CN or $NO_2$; and W is O or S.

The formula I perfluoroalkanoyl aminonitrile is useful in the preparation of 2-perfluoroalkyl-3-oxazolin-5-one which is a key intermediate in the manufacture of insecticidal, acaricidal and nematocidal pyrrole compounds. The preparation of 2-perfluoroalkyl-3-oxazolin-5-one is described in co-pending patent application Ser. No. 175,822, (Attorney Docket No. 32,356) filed concurrently herewith.

DETAILED DESCRIPTION OF THE INVENTION

Arylpyrrole compounds, particularly 2-aryl-5-trifluoromethylpyrrole-3-carbonitrile compounds are a new class of highly effective insecticidal, acaricidal and nematocidal agents. A key intermediate in their preparation is the 2-perfluoroalkyl-3-oxazolin-5-one compound of formula II

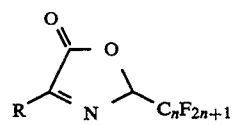 (II)

wherein n and R are as described hereinabove for formula I. Methods currently known to prepare the formula II oxazolinone involve the preparation of the appropriate arylglycine V via hydrolysis of the aminonitrile III. The aminonitrile is obtained via the Strecker synthesis from the appropriate aldehyde (W. L. Matier et al, J. Med. Chem., 1973, 16,901). Protection of the amino group in the aminonitrile III by acetylation to VI followed by acidic hydrolysis of both the cyano and the protecting groups is required due to the instability of the aminonitrile III under hydrolysis conditions. The thus-obtained glycine V is then trifluoroacetylated to give VII and cyclized to give the desired oxazolinone II in 4 steps. This procedure is shown in flow diagram I, wherein R is p-chlorophenyl and n is 1.

FLOW DIAGRAM I

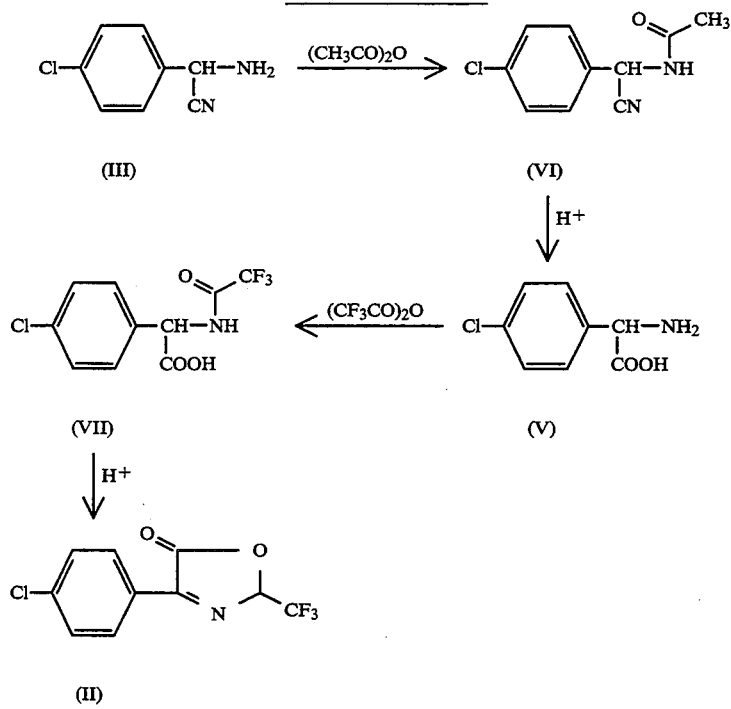

It has now been found that direct perfluoroacylation of the Strecker product III gives the perfluoroalkanoyl aminonitrile I which may be readily converted to the desired 2-perfluoroalkyl-3-oxazolin-5one II. The reaction is shown in flow diagram II wherein m is 1 or 2, X is Cl, $OR_1$ or O and $R_1$ is hydrogen or $C_1$–$C_6$alkyl with the proviso that when X is O, then m must be 2 and when X is Cl or $OR_1$, then m must be 1.

FLOW DIAGRAM II

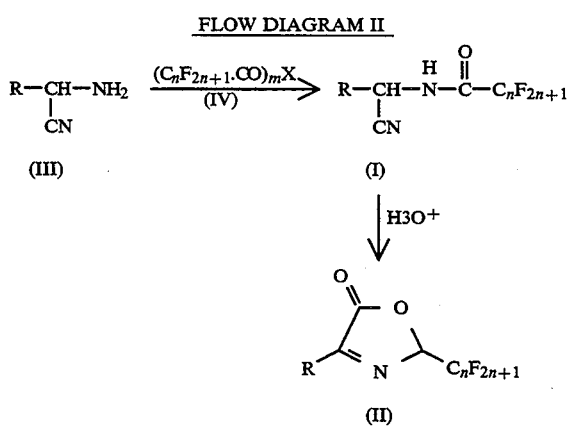

Surprisingly, the perfluoroalkanoyl aminonitrile of formula I may be cyclized in a single step in good yield under aqueous acid conditions to the 2-perfluoroalkyl-3-oxazolin-5-one compound of formula II.

Preferred compounds of formula I are those wherein n is 1, 2 or 3 and more preferred are those wherein n is 1. Also preferred are those compounds of formula I wherein R is phenyl optionally substituted with one to three halogen, $NO_2$, $C_1$–$C_4$haloalkyl or $C_1$–$C_4$haloalkoxy groups.

In accordance with the method of invention, an aminonitrile of formula III is admixed with approximately an equimolar amount of a perfluoroacylating agent of formula IV in the presence of a solvent, optionally in the presence of a base, to form the perfluoroalkanoyl aminonitrile of formula I. The formula I compound is then cyclized in the presence of an aqueous acid to form the formula II compound, 2-perfluoralkyl-3-oxazolin-5 one.

Solvents suitable for use in the method of invention are aromatic hydrocarbons, or halogenated aromatic hydrocarbons, preferably aromatic hydrocarbons such as toluene, benzene, xylene and the like, more preferrably, toluene.

Acids suitable for use in the method of invention include sulfuric acid, methanesulfonic acid benzenesulfonic acid, p-toluenesulfonic acid, naphthalenesulfonic acid, fluoroboric acid, boron trifluoride complexes and the like. Boron trifluoride complexes may include $BF_3$ etherate, $BF_3$ methanol complex, $BF_3$ ethanol complex, $BF_3$ dihydrate and the like. Water may be introduced as a hydrate, i.e. p-toluensulfonic acid monohydrate or as a solute such as 30%–60% aqueous sulfuric acid.

In actual practice, if a perfluoroacyl chloride, such as trifluoroacetyl chloride, is used as the formula IV reagent, then an equimolar amount of a base may be added as an HCl scavenger. Among the bases which may be used are alkali metal carbonates such as sodium carbonate or potassium carbonate or alkali metal bicarbonates such as sodium or potassium bicarbonate or mixtures thereof or tertiary amines.

Tertiary amines suitable for use in the method of invention are any of those well known in the art such as trialkylamine, dialkylarylamine, triarylamine, and the like preferably trialkylamine, more preferably triethylamine.

In order to provide a more clear understanding of the invention, the following examples are set forth below. These examples are merely illustrative and are not to be understood to limit the scope or underlying principles of the invention in any way.

The terms $^1$H, $^{13}$C and $^{19}$FNMR designate proton, carbon 13 and fluorine 19 nuclear magnetic resonance, respectively.

EXAMPLE 1

Preparation of N-[(p-Chlorophenyl)cyanomethyl]-2,2,2-trifluoroacetamide

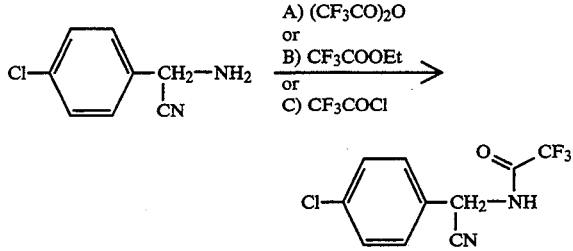

Method A:

A stirred slurry of α-cyano-p-chlorobenzylamine (250 g, 1.5 mol) in toluene is treated with trifluoroacetic anhydride (315 g, 1.5 mol) at 35° C. over a 90 minute period. The mixture is treated with heptane, the resultant precipitate is filtered and the filter-cake is washed with toluene/heptane to give the title product, 323.7 g, 82% yield, mp 127°–128° C., identified by $^1$H, $^{13}$C and $^{19}$FNMR analyses.

Method B:

A solution of α-cyano-p-chlorobenzylamine (83.3 g, 0.5 mol) in methanol is treated with ethyl trifluoroacetate (85.2 g, 0.6 mol), stirred at room temperature for about 16 hours and concentrated in vacuo to give a residue. The residue is crystallized from toluene/heptane to give the title product as a pale yellow solid, 88.3 g, 67.2% yield, mp 127°–128° C.

Method C:

A mixture of α-cyano-p-chlorobenzylamine (83.3 g, 0.5 mol) and triethylamine (50.6 g, 0.5 mol) toluene is treated dropwise with trifluoroacetyl chloride (66.2 g, 0.5 mol), stirred at ambient temperature for about 1 hour and filtered. The filtrate is washed once with water and concentrated in vacuo to give a residue. The residue is crystallized in toluene/hexane to give the title product, 114.2 g, 87% yield, mp 127°–128° C.

EXAMPLE 2

Preparation of N-(Arylcyanomethyl)-2,2,2-trifluoroacetamide

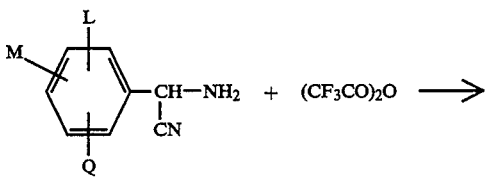

Using essentially the same procedure described as Method A in Example 1 and substituting the appropriate α-cyanobenzylamine as starting material, the following N-(arylcyanomethyl) 2,2,2-trifluoroacetamide products are obtained. The products are identified by $^1$H, $^{13}$C and $^{19}$FNMR analyses.

TABLE I

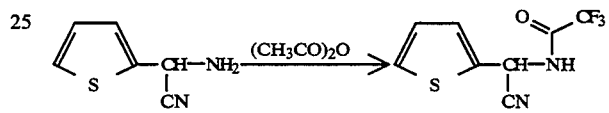

| L | M | Q | mp °C. | % Yield |
|---|---|---|---|---|
| H | 4-Br | H | 128.0–128.5 | 76 |
| H | 4-CF$_3$ | H | 115.0–116.0 | 63 |
| 3-Cl | 4-Cl | H | 113.0–115.0 | 35[a] |

[a]Based on aldehyde used in Strecker synthesis. (Crude Strecker product used as starting material)

EXAMPLE 3

Preparation of N-(α-Cyanothienyl)-2,2,2-trifluoroacetamide

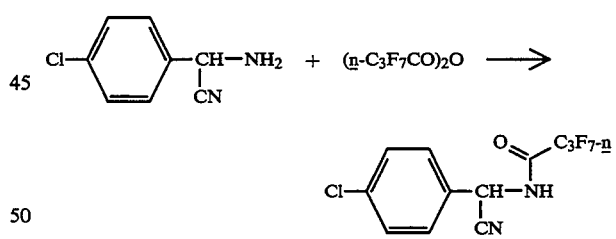

Using essentially the same procedure described as Method A in Example 1 and substituting the crude Strecker product, α-cyano-2-thiophenemethylamine, as starting material the title product is obtained in 23% yield[a], m.p. 73.0°–74.5° C., identified by $^1$H, $^{13}$C and $^{19}$FNMR analyses.

[a]Based upon starting aldehyde used in Strecker synthesis.

EXAMPLE 4

Preparation of N-[(p-Chlorophenyl)cyanomethyl]-2,2,3,3,4,4,4-heptafluorobutyramide

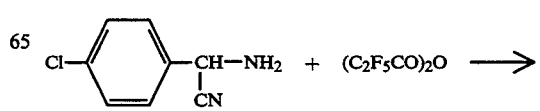

Using essentially the same procedure described as Method A in Example 1 and substituting heptafluorobutyric anhydride as the perfluoro-acylating agent, the title product is obtained as white crystals in 95% yield, mp 93.0°–95.0° C., identified by $^1$H $^{13}$C and $^{19}$FNMR analyses.

EXAMPLE 5

Preparation of N-[(p-Chlorophenyl)cyanomethyl]-2,2,3,3,3-pentafluoropropionamide -continued

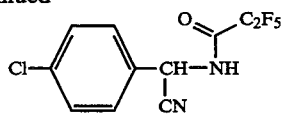

Using essentially the same procedure described as Method A in Example 1 and substituting pentafluoropropionic anhydride as the perfluoro-acylating agent, the title product is obtained as white crystals, 95% yield, mp 118.0°–118.5° C., identified by $^1H$, $^{13}C$ and 19FNMR analyses.

EXAMPLE 6

Preparation of 4-(p-Chlorophenyl-2-(trifluoromethyl)-3-oxazolin-5-one

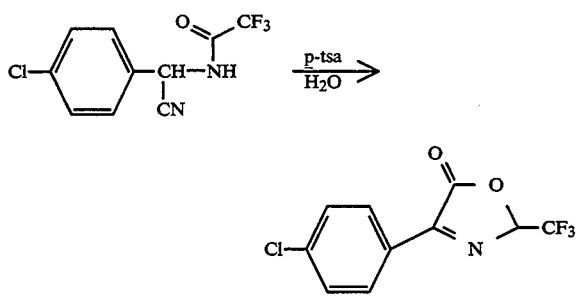

Method A:

A solution of N-[(p-chlorophenyl)cyanomethyl]-2,2,2-trifluoroacetamide (0.1 lmol ) in toluene at 80° C. is treated portion-wise with p-toluene sulfonic acid monohydrate (p-tsa.$H_2O$ )(0.11 mol) over an 0.75–1.0 hour period, stirred at 90°–95° C. for 2–3 hours, cooled and filtered. The filtrate is washed twice with water and concentrated in vacuo to give an oil residue. The oil is dissolved in heptane, filtered and the filtrate is vacuum distilled to give the title product as an oil, 55.6% yield, bp 78° C./0.01 mmHg, identified by $^1H$, $^{13}C$ and $^{19}F$NMR analyses.

Method B:

A solution of N-[p-(chlorophenyl)cyanomethyl]-2,2,2-trifluoroacetamide (26.3 g, 0.1 mol) in toluene and methanesulfonic acid (10.7 g, 0.11 mol) at 80° C. is treated with water (2 mL, 0.11 mol) over a 20 minute period, stirred at 90° C. for 8 hours and cooled. The reaction mixture is washed twice with water. The organic layer is concentrated in vacuo to give an oil which is vacuum distilled to give the title product as an oil, 13.7 g, bp 80° C./0.01 mm Hg.

EXAMPLE 7

Preparation of 4-(2-Thienyl-2-(trifluoromethyl)-3-oxazolin-5-one

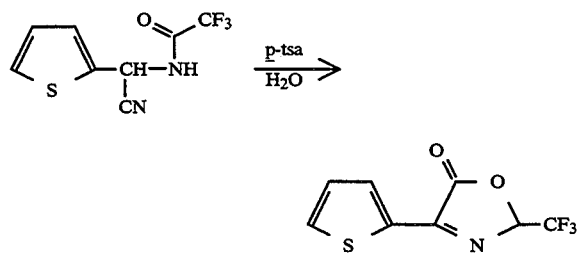

Using essentially the same procedure described as Method A in Example 6 and substituting N-(α-cyanothienyl)-2,2,2-trifluoroacetamide as starting material, the title product is obtained as a pale brown solid, 50% yield, mp 62.0°–65.0° C., identified by IR and $^1H$, $^{13}C$ and $^{19}F$NMR analyses.

EXAMPLE 8

Preparation of 2-perfluoroalkyl-3-oxazlin-5-one

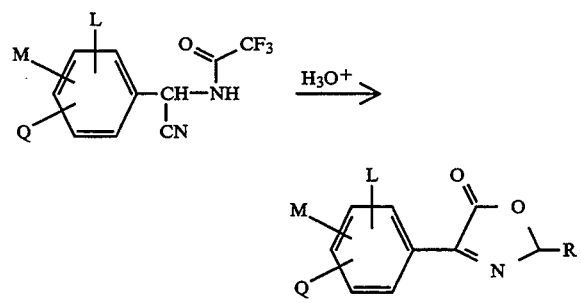

Using essentially the same procedure described as Method A in Example 6 and substituting the appropriate perfluoroalkyanoyl aminonitrile as starting material, the compounds shown in Table II are obtained.

TABLE II

| L | M | Q | R | mp °C. | % Yield |
|---|---|---|---|--------|---------|
| H | 4-Br | H | $CF_3$ | 48.0–51.0 | 64 |
| H | 4-$CF_3$ | H | $CF_3$ | 39.0–40.5 | 55 |
| 3-Cl | 4-Cl | H | $CF_3$ | 103°/0.1 mm$^a$ | 54 |
| H | 4-Cl | H | $C_2F_5$ | 39.0–42.0 | 72 |
| H | 4-Cl | H | n-$C_3H_7$ | 93.0–95.0 | 56 |

$^a$bp °C.

I claim

1. A compound having formula I $$R-\underset{\underset{CN}{|}}{CH}-NH-\overset{\overset{O}{\|}}{C}-C_nF_{2n+1} \qquad (I)$$

wherein n is an integer of 1, 2, 3, 4, 5, 6, 7 or 8;

R is 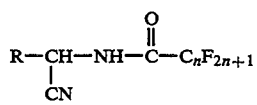

L is hydrogen or halogen;

M and Q are each independently hydrogen, halogen, CN, $NO_2$, $C_1$-$C_4$alkyl, $C_1$-$C_4$haloalkoxy, $C_1$-$C_4$alkylthio, or when M and Q are on adjacent positions they may be taken together with the carbon atoms to which they are attached to form a ring in which MQ represents the structure

—CH=CH—CH=CH— with the proviso that at least one of L, M and Q must be other than hydrogen.

2. The compound according to claim 1 wherein n is an integer of 1 or 2.

3. The compound according to claim 2 wherein

R is 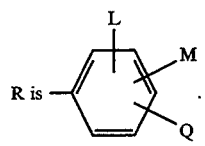

4. The compound according to claim 3 wherein L is hydrogen and M and Q are each independently hydrogen, halogen or $C_1$–$C_4$ haloalkyl.

5. The compound according to claim 4 N-[(p-chlorophenyl)cyanomethyl]-2,2,2-trifluoroacetamide.

6. The compound according to claim 4 N-[(p-bromophenyl)cyanomethyl]-2,2,2-trifluoroacetamide.

7. The compound according to claim 4 N-[(3,4-dichlorophenyl)cyanomethyl]-2,2,2-trifluoroacetamide.

8. The compound according to claim 4 N-[(3,5-dichlorophenyl)cyanomethyl]-2,2,2-trifluoroacetamide.

9. The compound according to claim 4 N-[($\alpha,\alpha,\alpha$-trifluoro-p-tolyl)cyanomethyl]-2,2,2-trifluoroacetamide.

10. The compound according to claim 4 N-[(p-chlorophenyl)cyanomethyl]-2,2,3,3,3-pentafluropropionamide.

* * * * *